United States Patent [19]
Outtrup

[11] Patent Number: 5,856,167
[45] Date of Patent: Jan. 5, 1999

[54] HYPOCHLORITE STABLE PROTEASE FROM BACILLUS SP., DSM 8473

[75] Inventor: Helle Outtrup, Ballerup, Denmark

[73] Assignee: Novo Nordisk A/S, Bagsvaerd, Denmark

[21] Appl. No.: 596,161

[22] PCT Filed: Sep. 2, 1994

[86] PCT No.: PCT/DK94/00331

§ 371 Date: Feb. 14, 1996

§ 102(e) Date: Feb. 14, 1996

[87] PCT Pub. No.: WO95/07350

PCT Pub. Date: Mar. 16, 1995

[30] Foreign Application Priority Data

Sep. 9, 1993 [DK] Denmark .................. 1008/93

[51] Int. Cl.$^6$ .............. C12N 9/54; C12N 9/52; C11O 3/386
[52] U.S. Cl. .......... 435/221; 435/220; 510/300; 510/305; 510/306
[58] Field of Search .............. 435/221, 220; 510/300, 305, 306

[56] References Cited

U.S. PATENT DOCUMENTS 5,118,623  6/1992  Boguslawski et al. .............. 435/222
5,358,865  10/1994  Outtrup et al. .................. 435/221

FOREIGN PATENT DOCUMENTS

88/01293  2/1988  WIPO .
92/07067  4/1992  WIPO .

OTHER PUBLICATIONS

Koltukova et al. (1985) Prikl. Biokhim. Microbiol., 21(4), "Some Physiochemical Properties of *Bacillus mesentericus* Proteinases", pp. 495–500, with English abstract.

Kalebina et al. (1983) Bioorg. Khim., 9(6), "Extracellular Serine Protease from *Bacillus brevis* –an Analog of Subtilisin BPN", pp. 815–823, with English abstract.

Chestukhina et al. (1982) Bioorg. Khim., 8(12), "Thiol Dependent Serine Proteinases 2: Extracellular Serine Proteinases", pp. 1649–1658, with English abstract.

Kalebina et al. (1988) Appl. Microbiol. Biotechnol., 28(6), "Serine Proteinase from *Bacillus brevis* : Lytic Action on Intact Yeast Cells", pp. 531–536.

Saravani et al. (1989) Biochem. Journal, 262(2), "Caldolase, A Chelator–Insensitive Extracellular Serine Proteinase from a *Thermus spp.* ", pp. 409–416.

Burton et al. (1993) Journal Gen. Microbiol., 139(6), "Purification and Characterization of a Serine Proteinase from Senescent Sporophores of the Commercial Mushroom *Agaricus–bisporus*", pp. 1379–1386.

*Primary Examiner*—Jon P. Weber
*Attorney, Agent, or Firm*—Steve T. Zelson; Elias J. Lambiris; Carol E. Rozek

[57] ABSTRACT

A protease obtained from Bacillus sp., DSM 8473, is disclosed which has improved hypochlorite stability as compared to other known proteases. The protease is suitable as a detergent additive and may be used singly or combined with other know enzymes in detergent compositions. A process for washing soiled fabric with detergent compositions containing the hypochlorite stable protease is also disclosed.

7 Claims, 2 Drawing Sheets

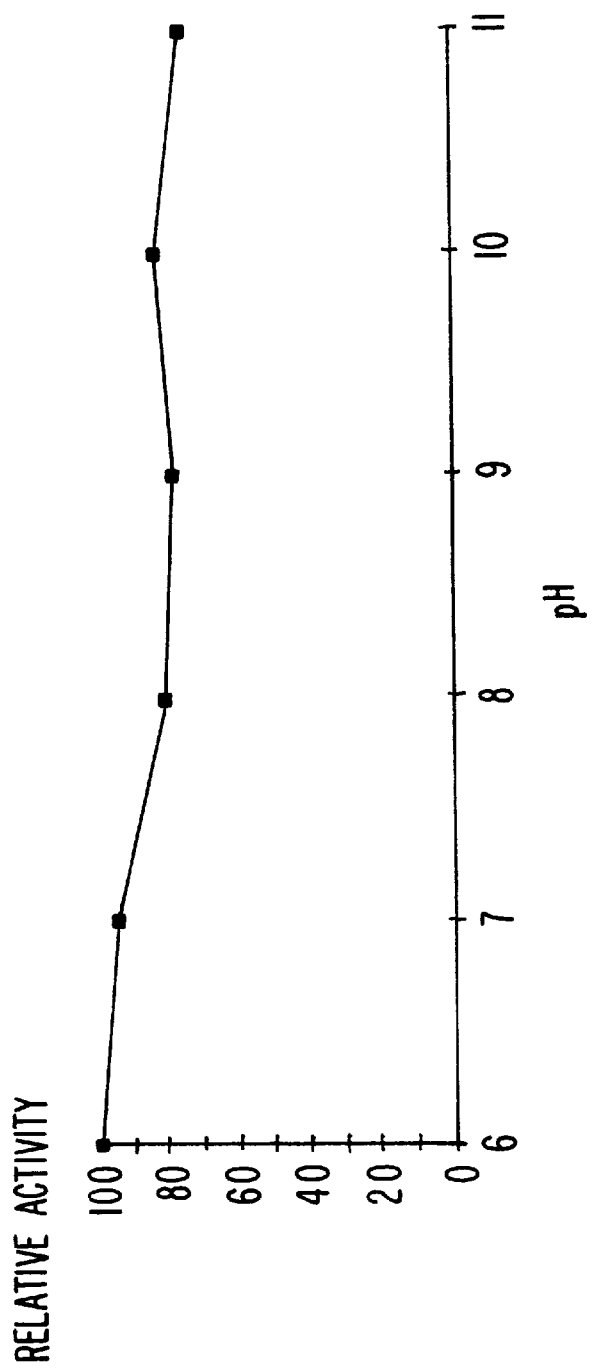

HYPOCHLORITE STABLE PROTEASE FROM BACILLUS SP., DSM 8473

CROSS-REFERENCE TO RELATED APPLICATIONS

This application is a 371 of PCT/DK94/00331 filed Sep. 2, 1994, which is incorporated herein by reference.

FIELD OF INVENTION

This invention is in the field of proteases derived from strains of Bacillus sp. More specifically, the invention is directed towards a novel protease derived from a strain of a novel Bacillus sp., which is characterized by being stable in solutions containing hypochlorite and/or other oxidizing agents. Moreover, the invention is directed towards a process for the preparation of the protease, and the use of the protease in processes in which water containing hypochlorite is being used.

BACKGROUND OF THE INVENTION

Proteases have been marketed for more than 20 years for a lot of different purposes, the most important as being ingredients in detergents.

Proteases have been developed by isolation of proteases found in nature. Most commercially available proteases are obtained from the genus Bacillus. Currently new types of proteases enter the market, offering the possibility of giving a better cost/performance ratio at various specified conditions.

Examples of commercial Bacillus protease products are Alcalase®, Esperase®, Primase®, Savinase® and Durazyme® (a protein-engineered variant of Savinase), all available from Novo Nordisk A/S, Denmark. These and similar enzyme products from other commercial sources are active in detergent solutions, i.e. at pH values in the range from 8 to 11 and in the presence of sequestering agents, surfactants and bleaching agents such as sodium borate, but their activity decreases if the process water used contains hypochlorite. This is an increasing problem as more and more water in the industrialized world gets chlorinated.

SUMMARY OF THE INVENTION

It is an object of the present invention to provide novel proteases with improved stability performance in solutions containing hypochlorite.

Accordingly, in its first aspect, the invention provides a protease having immunochemical properties identical to those of a protease derived from the strain Bacillus sp., DSM 8473, the protease being stable in solutions containing hypochlorite.

In a second aspect, the invention relates to a biologically pure culture of a strain of a novel Bacillus sp. In a more specific aspect, the invention relates to a strain of Bacillus sp., DSM 8473, or a mutant or a variant thereof.

In a third aspect, the invention provides a process for the preparation of the protease, which process comprises cultivation of a protease producing strain of a novel Bacillus sp. in a suitable nutrient medium, containing carbon and nitrogen sources and inorganic salts, followed by recovery of the desired enzyme. In a more specific aspect, Bacillus sp., DSM 8473, or a mutant or a variant thereof encoding a protease having immunochemical properties identical to those of the protease derived from Bacillus sp., DSM 8473, is cultivated.

In a fourth aspect, the use of the protease in processes in which water containing hypochlorite is being used, is claimed.

BRIEF DESCRIPTION OF DRAWINGS

The present invention is further illustrated by reference to the accompanying drawings, in which

FIG. 2 shows the relation between pH and the proteolytic activity of a novel protease according to the invention (the protease preparation obtained according to Ex.1, with 2% of casein as substrate and at 25° C., using Britten-Robinson buffers adjusted to predetermined pH values in the pH range of from 6 to 11).

DETAILED DISCLOSURE OF THE INVENTION

The Microorganism

Figure 1:
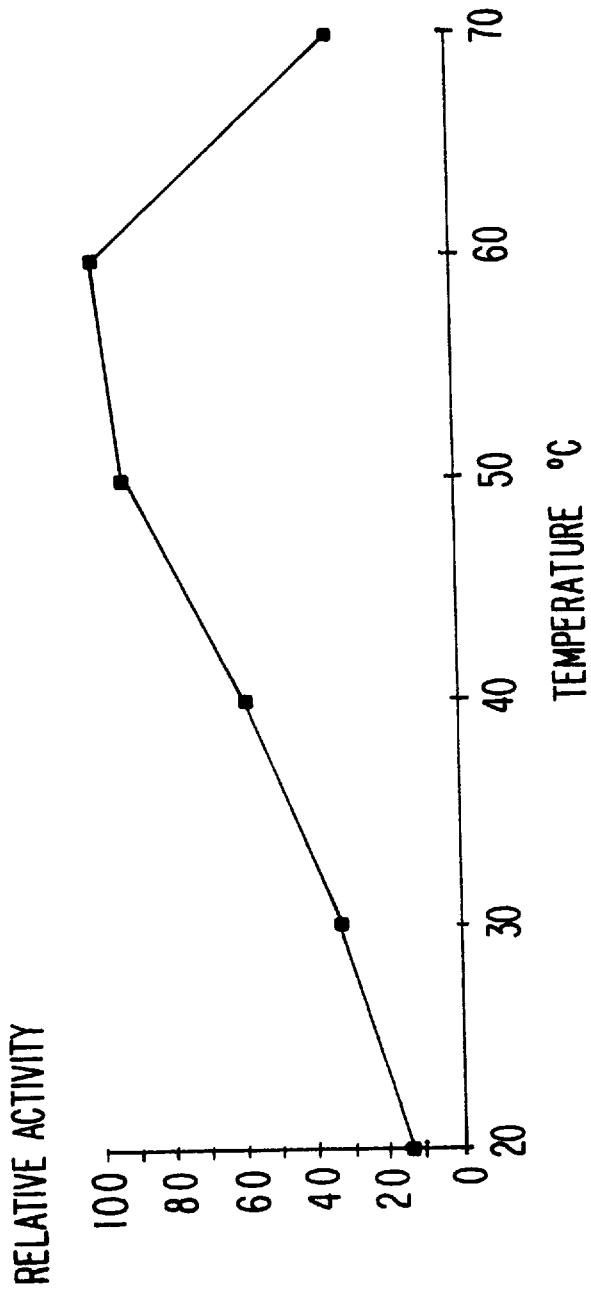
FIG. 1 shows the relation between temperature and the proteolytic activity of a novel protease according to the invention (the protease preparation obtained according to Ex.1, with 2% of casein as substrate and at pH 9.5).

The novel microorganism of the invention, able to produce an enzyme of the invention, is represented by the strain that was isolated from a soil sample.

The novel Bacillus sp. has been deposited according to the Budapest Treaty on the International Recognition of the Deposits of Microorganisms for the Purpose of Patent Procedures on 23 Aug. 1993, at Deutsche Sammlung von Mikroorganismen und Zellkulturen GmbH, under Accession No. DSM 8473.

The microorganism of this invention is an aerobic, spore forming bacterium belonging to the genus Bacillus. Morphologically it can be described as motile rods with a diameter of 0.6–0.8 μm, and a length of 1–3 μm. The spores are cylindrical to ellipsoid, not swelling the sporangium, central to subterminal. Optimum temperature for growth is within 30°–50° C., and optimal pH for growth is within 6–8, good growth at 50° C. The microorganism forms yellow colonies, only when grown at 37° C.—otherwise colourless, slimy colonies on nutrient agar slants, and no diffusion of pigment into the agar is observed.

Cultivation of the Microorganism

The microorganism of the invention can be cultivated under aerobic conditions in a nutrient medium containing assimilable carbon and nitrogen together with other essential nutrients, the medium being composed in accordance with the principles of the known art.

Suitable carbon sources are carbohydrates such as sucrose, glucose and starch, or carbohydrate containing materials such as cereal grain, malt, rice and sorghum. The carbohydrate concentration incorporated in the medium may vary widely, e.g. up to 25% and down to 1–5%, but usually 8–10% will be suitable, the percentages being calculated as equivalents of glucose.

The nitrogen source in the nutrient medium may be of inorganic and/or organic nature. Suitable inorganic nitrogen sources are nitrates and ammonium salts. Among the organic nitrogen sources quite a number are used regularly in fermentation processes involving the cultivation of bacteria. Illustrative examples are soybean meal, cotton seed meal, peanut meal, casein, corn, corn steep liquor, yeast extract, urea and albumin. In addition, the nutrient medium should also contain usual trace substances.

For cultivation in tank fermentors it is necessary to use artificial aeration. The rate of aeration is similar to that used in conventional tank fermentation.

After fermentation, liquid enzyme concentrates may be produced by removal of coarse material from the broth or, if desired, concentration of the broth by evaporation at low temperature or by reverse osmosis. Finally, preservatives may be added to the concentrate.

Solid enzyme preparations may be prepared from the purified and/or concentrated broth by precipitation with salts, such as $Na_2SO_4$ or water-miscible solvents, such as ethanol or acetone. Removal of the water in the broth by suitable drying methods, such as spray-drying, may also be employed.

Assay for Proteolytic Activity

The proteolytic activity is determined with casein as substrate. One Casein Protease Unit (CPU) is defined as the amount of enzyme liberating 1 mM of primary amino groups (determined by comparison with a serine standard) per minute under standard conditions, i.e. incubation for 30 minutes at 25° C. and pH 9.5.

The Enzymes

The enzymes of the invention are novel proteases. They are alkaline proteases, obtainable by cultivation of a microorganism of the invention, preferably Bacillus sp., DSM 8473, or a mutant or a variant thereof, in a suitable nutrient medium, containing carbon and nitrogen sources and inorganic salts. The enzymes can also be obtained by recombinant DNA-technology.

The proteases of the invention can be described by the following characteristics.

Physical-chemical Properties

A molecular weight of 30 kD, determined by SDS-PAGE. A pI of about 8.8 as determined by isoelectric focusing on LKB Ampholine® PAG plates.

The protease activity is inhibited by PMSF and Turkey-egg-white proteinase inhibitor. EDTA and soybean-protein inhibitor do not influence the protease activity.

The temperature activity relationship was determined with 2%. casein as substrate and at pH 9.5. The assay for proteolytic activity described previously was used with the modification that the incubation temperature was varied in the interval of from 15° to 70° C. The result for a novel protease is shown in FIG. 1. It appears from the figure that the protease possesses proteolytic activity at temperatures of from 15° C. to 70° C., and have a temperature optimum within the range of from 50° to 60° C., around 60° C.

The dependence of activity on pH was determined by the same procedure, using buffers adjusted to predetermined pH values in the pH range of from 6 to 11. The result is shown in FIG. 2. It appears from this figure that the enzyme possesses proteolytic activity at all pH values in this range (below 11 to above 6).

The proteases of the invention possess especial potentials in water containing hypochlorite. Ex. 2 illustrates this very clearly. In general the proteases have a residual activity of at least 45%, preferably above 60%, most preferably above 80% at 5 ppm NaOCl, and a residual activity of at least 10%, preferably above 20% at 10 ppm NaOCl.

Immunochemical Properties

The immunochemical properties can be determined immunologically by cross-reaction identity tests. The identity tests can be performed by the well-known Ouchterlony double immunodiffusion procedure or by tandem crossed immunoelectrophoresis according to I. M. Roitt; Immunology, Gower Medical Publishing (1985) and N. H. Axelsen; Handbook of Immunoprecipitation-in-Gel Techniques; Blackwell Scientific Publications (1983), Chapters 5 and 14. The terms "antigenic identity" and "partial antigenic identity" are described in the same book, Chapters 5, 19 and 20.

Monospecific antiserum was generated according to the above mentioned method by immunizing rabbits with one of the purified proteases of the invention. The immunogen was mixed with Freund's adjuvant and injected subcutaneously into rabbits every second week. Antiserum was obtained after a total immunization period of 8 weeks, and immunoglobulin was prepared therefrom as described by N. H. Axelsen, supra.

Ouchterlony double immunodiffusion tests showed immunochemical non-identity between the protease of the invention and the known alkaline serine proteases Savinase, Esperase, Durazyme, Primase (available from Novo Nordisk A/S), and Kazusase™ (available from SHOWA DENKO). A partial immunochemical identity was demonstrated with Alcalase from *Bacillus licheniformis*.

Oxidizing agents

The proteases of the invention are stable against oxidizing agents such as hypochlorite, hydrogen peroxide, and peroxide precursors (e.g. percarbonate, perborate and peroxycarboxylic acids such as peracetic acid).

Applications

The proteases of the invention may typically be added as components of detergent compositions. The proteases may also be useful in removal of proteinaceous soiling.

Furthermore, the novel proteases described in this invention may be used in the treatment of protein in process water containing hypochlorite, especially wherein the hypochlorite is present at a concentration of 1–10 ppm.

Deterrent Compositions

According to the invention, the protease may be added as a component of a detergent composition. As such, it may be included in the detergent composition in the form of a detergent additive. The detergent composition as well as the detergent additive may additionally comprise one or more other enzymes, such as lipases, amylases, cutinases, cellulases and oxidoreductases.

In a specific aspect, the invention provides a detergent additive. The enzymes may be included in a detergent composition by adding separate additives containing one or more enzymes, or by adding a combined additive comprising all of these enzymes. A detergent additive of the invention, i.e. a separated additive or a combined additive, can be formulated e.g. as granulates, liquids, slurries, etc. Preferred detergent additive formulations are granulates, in particular non-dusting granulates, liquids, in particular stabilized liquids, slurries, or protected enzymes.

Non-dusting granulates may be produced, e.g., as disclosed in U.S. Pat. Nos. 4,106,991 and 4,661,452 (both to Novo Industri A/S) and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in patent GB 1483591. Liquid enzyme preparations may, for instance, be stabilized by adding a polyol such as propylene glycol, a sugar or sugar alcohol, lactic acid or boric acid according to established methods. Other enzyme stabilizers are well known in the art. Protected enzymes may be prepared according to the method disclosed in EP 238,216.

The detergent composition of the invention may be in any convenient form, e.g. as powder, granules, paste or liquid. A liquid detergent may be aqueous, typically containing up to 70% water and 0–30% organic solvent, or nonaqueous.

The detergent composition comprises one or more surfactants, each of which may be anionic, nonionic, cationic, or zwitterionic. The detergent will usually contain 0–50% of anionic surfactant such as linear alkylbenzenesulfonate (LAS), alpha-olefinsulfonate (AOS), alkyl sulfate (fatty alcohol sulfate) (AS), alcohol ethoxysulfate (AEOS or AES), secondary alkanesulfonates (SAS), alpha-sulfo fatty acid methyl esters, alkyl- or alkenylsuccinic acid or soap. It may also contain 0–40% of nonionic surfactant such as alcohol ethoxylate (AEO or AE), carboxylated alcohol ethoxylates, nonylphenol ethoxylate, alkylpolyglycoside, alkyldimethylamineoxide, ethoxylated fatty acid monoethanolamide, fatty acid monoethanolamide, or polyhydroxy alkyl fatty acid amide (e.g. as described in WO 92/06154).

The detergent composition may additionally comprise one or more other enzymes, such as amylases, lipases, cutinases, cellulases and oxidoreductases.

The detergent may contain 1–65% of a detergent builder or complexing agent such as zeolite, diphosphate, triphosphate, phosphonate, citrate, nitrilotriacetic acid (NTA), ethylenediaminetetraacetic acid (EDTA), diethylenetriaminepentaacetic acid (DTMPA), alkyl- or alkenylsuccinic acid, soluble silicates or layered silicates (e.g. SKS-6 from Hoechst). The detergent may also be unbuilt, i.e. essentially free of detergent builder.

The detergent may comprise one or more polymers. Examples are carboxymethylcellulose (CMC), poly(vinylpyrrolidone) (PVP), polyethyleneglycol (PEG), poly(vinyl alcohol) (PVA), polycarboxylates such as polyacrylates, maleic/acrylic acid copolymers and lauryl methacrylate/acrylic acid copolymers.

The detergent may contain a bleaching system which may comprise a $H_2O_2$ source such as perborate or percarbonate which may be combined with a peracid-forming bleach activator such as tetraacetylethylenediamine (TAED) or nonanoyloxybenzenesulfonate (NOBS). Alternatively, the bleaching system may comprise peroxyacids of e.g. the amide, imide, or sulfone type.

The enzymes of the detergent composition of the invention may be stabilized using conventional stabilizing agents, e.g. a polyol such as propylene glycol or glycerol, a sugar or sugar alcohol, lactic acid, boric acid, or a boric acid derivative as e.g. an aromatic borate ester, and the composition may be formulated as described in e.g. WO 92/19709 and WO 92/19708.

The detergent may also contain other conventional detergent ingredients such as e.g. fabric conditioners including clays, foam boosters, suds suppressors, anti-corrosion agents, soil-suspending agents, anti-soil redeposition agents, dyes, bactericides, optical brighteners, or perfume.

The pH (measured in aqueous solution at use concentration) will usually be neutral or alkaline, e.g. 7–11.

Particular forms of detergent compositions within the scope of the invention include:

1) A detergent composition formulated as a granulate having a bulk density of at least 600 g/l comprising

| | |
|---|---|
| linear alkylbenzenesulfonate (calculated as acid) | 7–12% |
| alcohol ethoxysulfate (e.g. $C_{12-18}$ alcohol, 1–2 EO) or alkyl sulfate (e.g. $C_{16-18}$) | 1–4% |
| alcohol ethoxylate (e.g. $C_{14-15}$ alcohol, 7 EO) | 5–9% |
| sodium carbonate (as $Na_2CO_3$) | 14–20% |
| soluble silicate (as $Na_2O, 2SiO_2$) | 2–6% |
| zeolite (as $NaAlSiO_4$) | 15–22% |
| sodium sulfate (as $Na_2SO_4$) | 0–6% |
| sodium citrate/citric acid (as $C_6H_5Na_3O_7/C_6H_8O_7$) | 0–15% |
| sodium perborate (as $NaBO_3.H_2O$) | 11–18% |
| TAED | 2–6% |
| carboxymethylcellulose | 0–2% |
| polymers (e.g. maleic/acrylic acid copolymer, PVP, PEG) | 0–3% |
| enzymes | 0–5% |
| minor ingredients (e.g. suds suppressors, perfume, optical brightener, photobleach) | 0–5% |

2) A detergent composition formulated as a granulate having a bulk density of at least 600 g/l comprising

| | |
|---|---|
| linear alkylbenzenesulfonate (calculated as acid) | 6–11% |
| alcohol ethoxysulfate (e.g. $C_{12-18}$ alcohol, 1–2 EO) or alkyl sulfate (e.g. $C_{16-18}$) | 1–3% |
| alcohol ethoxylate (e.g. $C_{14-15}$ alcohol, 7 EO) | 5–9% |
| sodium carbonate (as $Na_2CO_3$) | 15–21% |
| soluble silicate (as $Na_2O, 2SiO_2$) | 1–4% |
| zeolite (as $NaAlSiO_4$) | 24–34% |
| sodium sulfate (as $Na_2SO_4$) | 4–10% |
| sodium citrate/citric acid (as $C_6H_5Na_3O_7/C_6H_8O_7$) | 0–15% |
| carboxymethylcellulose | 0–2% |
| polymers (e.g. maleic/acrylic acid copolymer, PVP, PEG) | 1–6% |
| enzymes | 0–5% |
| minor ingredients (e.g. suds suppressors, perfume) | 0–5% |

3) A detergent composition formulated as a granulate having a bulk density of at least 600 g/l comprising

| | |
|---|---|
| linear alkylbenzenesulfonate (calculated as acid) | 5–9% |
| alcohol ethoxylate (e.g. $C_{12-15}$ alcohol, 7 EO) | 7–14% |
| soap as fatty acid (e.g. $C_{16-22}$) | 1–3% |
| sodium carbonate (as $Na_2CO_3$) | 10–17% |
| soluble silicate (as $Na_2O, 2SiO_2$) | 3–9% |
| zeolite (as $NaAlSiO_4$) | 23–33% |
| sodium sulfate (as $Na_2SO_4$) | 0–4% |
| sodium perborate (as $NaBO_3H_2O$) | 8–16% |
| TAED | 2–8% |
| phosphonate (e.g. EDTMPA) | 0–1% |
| carboxymethylcellulose | 0–2% |
| polymers (e.g. maleic/acrylic acid copolymer, PVP, PEG) | 0–3% |
| enzymes | 0–5% |
| minor ingredients (e.g. suds suppressors, perfume, optical brightener) | 0–5% |

4) A detergent composition formulated as a granulate having a bulk density of at least 600 g/l comprising

| | |
|---|---|
| linear alkylbenzenesulfonate (calculated as acid) | 8–12% |
| alcohol ethoxylate (e.g. $C_{12-15}$ alcohol, 7 EO) | 10–25% |
| sodium carbonate (as $Na_2CO_3$) | 14–22% |
| soluble silicate (as $Na_2O, 2SiO_2$) | 1–5% |
| zeolite (as $NaAlSiO_4$) | 25–35% |

-continued

| | |
|---|---|
| sodium sulfate (as Na$_2$SO$_4$) | 0–10% |
| carboxymethylcellulose | 0–2% |
| polymers (e.g. maleic/acrylic acid copolymer, PVP, PEG) | 1–3% |
| enzymes | 0–5% |
| minor ingredients (e.g. suds suppressors, perfume) | 0–5% |

5) An aqueous liquid detergent composition comprising

| | |
|---|---|
| linear alkylbenzenesulfonate (calculated as acid) | 15–21% |
| alcohol ethoxylate (e.g. C$_{12-15}$ alcohol, 7 EO or C$_{12-15}$ alcohol, 5 EO) | 12–18% |
| soap as fatty acid (e.g. oleic acid) | 3–13% |
| alkenylsuccinic acid (C$_{12-14}$) | 0–13% |
| aminoethanol | 8–18% |
| citric acid | 2–8% |
| phosphonate | 0–3% |
| polymers (e.g. PVP, PEG) | 0–3% |
| borate (as B$_4$O$_7$) | 0–2% |
| ethanol | 0–3% |
| propylene glycol | 8–14% |
| enzymes | 0–5% |
| minor ingredients (e.g. dispersants, suds suppressors, perfume, optical brightener) | 0–5% |

6) An aqueous structured liquid detergent composition comprising

| | |
|---|---|
| linear alkylbenzenesulfonate (calculated as acid) | 15–21% |
| alcohol ethoxylate (e.g. C$_{12-15}$ alcohol, 7 EO or C$_{12-15}$ alcohol, 5 EO) | 3–9% |
| soap as fatty acid (e.g. oleic acid) | 3–10% |
| zeolite (as NaAlSiO$_4$) | 14–22% |
| potassium citrate | 9–18% |
| borate (as B$_4$O$_7$) | 0–2% |
| carboxymethylcellulose | 0–2% |
| polymers (e.g PEG, PVP) | 0–3% |
| anchoring polymers as e.g. lauryl methacrylate/acrylic acid copolymer; molar ratio 25:1; MW 3800 | 0–3% |
| glycerol | 0–5% |
| enzymes | 0–5% |
| minor ingredients (e.g. dispersants, suds suppressors, perfume, optical brighteners) | 0–5% |

7) A detergent composition formulated as a granulate having a bulk density of at least 600 g/l comprising

| | |
|---|---|
| fatty alcohol sulfate | 5–10% |
| ethoxylated fatty acid monoethanolamide | 3–9% |
| soap as fatty acid | 0–3% |
| sodium carbonate (as Na$_2$CO$_3$) | 5–10% |
| soluble silicate (as Na$_2$O, 2SiO$_2$) | 1–4% |
| zeolite (as NaAlSiO$_4$) | 20–40% |
| sodium sulfate (as Na$_2$SO$_4$) | 2–8% |
| sodium perborate (as NaBO$_3$.H$_2$O) | 12–18% |
| TAED | 2–7% |
| polymers (e.g. maleic/acrylic acid copolymer, PEG) | 1–5% |
| enzymes | 0–5% |
| minor ingredients (e.g. optical brightener, suds suppressors, perfume) | 0–5% |

8) A detergent composition formulated as a granulate comprising

| | |
|---|---|
| linear alkylbenzenesulfonate (calculated as acid) | 8–14% |
| ethoxylated fatty acid monoethanolamide | 5–11% |
| soap as fatty acid | 0–3% |
| sodium carbonate (as Na$_2$CO$_3$) | 4–10% |
| soluble silicate (as Na$_2$O, 2SiO$_2$) | 1–4% |
| zeolite (as NaAlSiO$_4$) | 30–50% |
| sodium sulfate (as Na$_2$SO$_4$) | 3–11% |
| sodium citrate (as C$_6$H$_5$Na$_3$O$_7$) | 5–12% |
| polymers (e.g. PVP, maleic/acrylic acid copolymer, PEG) | 1–5% |
| enzymes | 0–5% |
| minor ingredients (e.g. suds suppressors, perfume) | 0–5% |

9) A detergent composition formulated as a granulate comprising

| | |
|---|---|
| linear alkylbenzenesulfonate (calculated as acid) | 6–12% |
| nonionic surfactant, | 1–4% |
| soap as fatty acid | 2–6% |
| sodium carbonate (as Na$_2$CO$_3$) | 14–22% |
| zeolite (as NaAlSiO$_4$) | 18–32% |
| sodium sulfate (as Na$_2$SO$_4$) | 5–20% |
| sodium citrate (as C$_6$H$_5$Na$_3$O$_7$) | 3–8% |
| sodium perborate (as NaBO$_3$.H$_2$O) | 4–9% |
| bleach activator (e.g. NOBS or TAED) | 1–5% |
| carboxymethylcellulose | 0–2% |
| polymers (e.g. polycarboxylate or PEG) | 1–5% |
| enzymes | 0–5% |
| minor ingredients (e.g. optical brightener, perfume) | 0–5% |

10) An aqueous liquid detergent composition comprising

| | |
|---|---|
| linear alkylbenzenesulfonate (calculated as acid) | 15–23% |
| alcohol ethoxysulfate (e.g. C$_{12-15}$ alcohol, 2–3 EO) | 8–15% |
| alcohol ethoxylate (e.g. C$_{12-15}$ alcohol, 7 EO or C$_{12-15}$ alcohol, 5 EO) | 3–9% |
| soap as fatty acid (e.g. lauric acid) | 0–3% |
| aminoethanol | 1–5% |
| sodium citrate | 5–10% |
| hydrotrope (e.g. sodium toluenesulfonate) | 2–6% |
| borate (as B$_4$O$_7$) | 0–2% |
| carboxymethylcellulose | 0–1% |
| ethanol | 1–3% |
| propylene glycol | 2–5% |
| enzymes | 0–5% |
| minor ingredients (e.g. polymers, dispersants, perfume, optical brighteners) | 0–5% |

11) An aqueous liquid detergent composition comprising

| | |
|---|---|
| linear alkylbenzenesulfonate (calculated as acid) | 20–32% |
| alcohol ethoxylate (e.g. C$_{12-15}$ alcohol, 7 EO or C$_{12-15}$ alcohol, 5 EO) | 6–12% |
| aminoethanol | 2–6% |
| citric acid | 8–14% |
| borate (as B$_4$O$_7$) | 1–3% |
| polymer (e.g. maleic/acrylic acid copolymer, anchoring polymers as e.g. lauryl methacrylate/acrylic acid copolymer and CMC) | 0–3% |
| glycerol | 3–8% |

-continued

| | |
|---|---|
| enzymes | 0–5% |
| minor ingredients (e.g. hydrotropes, dispersants, perfume, optical brighteners) | 0–5% |

12) A detergent composition formulated as a granulate having a bulk density of at least 600 g/l comprising

| | |
|---|---|
| anionic surfactant (linear alkylbenzenesulfonate, alkyl sulfate, alpha-olefinsulfonate, alpha-sulfo fatty acid methyl esters, alkanesulfonates, soap) | 25–40% |
| nonionic surfactant (e.g. alcohol ethoxylate) | 1–10% |
| sodium carbonate (as $Na_2CO_3$) | 8–25% |
| soluble silicates (as $Na_2O, 2SiO_2$) | 5–15% |
| sodium sulfate (as $Na_2SO_4$) | 0–5% |
| zeolite (as $NaAlSiO_4$) | 15–28% |
| sodium perborate (as $NaBO_3.4H_2O$) | 0–20% |
| bleach activator (TAED or NOBS) | 0–5% |
| enzymes | 0–5% |
| minor ingredients (e.g. perfume, optical brighteners) | 0–3% |

13) Detergent formulations as described in 1)–12) where the content of linear alkylbenzenesulfonate—or a part of it—is substituted by alkyl sulfate ($C_{12}$–$C_{18}$).

14) Detergent formulations as described in 1)–13) which contain a stabilized or encapsulated peracid either as an additional component or as a substitute for already specified bleach systems.

15) Detergent compositions as described in 1), 3), 7), 9) and 12) where the content of perborate is substituted with percarbonate.

16) Detergent compositions as described in 1), 3), 7), 9) and 12) which additionally contains a Manganese catalyst. The Manganese catalyst may e.g. be one of the compounds described in "Efficient manganese catalysts for low-temperature bleaching", Nature 369, 1994, pp. 637–639.

17) Detergent composition formulated as a nonaqueous detergent liquid comprising a liquid nonionic surfactant as e.g. linear alkoxylated primary alcohol, a builder system (e.g. phosphate), enzyme and alkali. The detergent may also comprise anionic surfactant and/or a bleach system.

The present invention is further illustrated in the following examples which are not in any way intended to limit the scope of the invention as claimed.

EXAMPLE 1

Bacillus sp., DSM 8473, was cultivated at 37° C. on a rotary shaking table (300 r.p.m.) in 500 ml baffled Erlenmeyer flasks containing 100 ml of medium of the following composition (per litre):

| | |
|---|---|
| Potato starch | 100 g |
| Ground barley | 50 g |
| Soybean flour | 20 g |
| $Na_2HPO_4 \times 12 H_2O$ | 9 g |
| Pluronic ® | 0.1 g |
| Sodium caseinate | 10 g |

The starch in the medium was liquified with α-amylase, and the medium was sterilized by heating at 120° C. for 45 minutes.

After 3 days of incubation the proteolytic activity of the culture was determined using the method described above.

After cultivation, the enzyme activity of the broth was 120 CPU/l.

After separation of the solid material the protease was purified by a conventional chromatographic method and then freeze-dried. The freeze-dried preparation had an activity of 7.4 CPU/g.

The characteristics of the preparation prepared in accordance with this Example have been referred to earlier in this specification, and reference is made hereto.

EXAMPLE 2

Stability Performance

The stability performance tests were conducted in 1.1 g/l of a commercial American powder detergent dissolved in approx. 6° dH (German Hardness) water with different concentrations of sodium hypochlorite at 25° C., isothermally for 60 minutes, with a protease concentration of 0.3 CPU per litre.

The results of these tests are shown in table 1 below:

TABLE 1

| | 0 ppm NaOCl | 5 ppm NaOCl | 10 ppm NaOCl |
|---|---|---|---|
| Alcalase | 100% | 10% | 0% |
| Primase | 100% | 5% | 0% |
| Esperase | 55% | 0% | 0% |
| Savinase | 100% | 0% | 0% |
| Durazyme | 100% | 40% | 0% |
| NOVEL PROTEASE | 100% | 100% | 30% |

Table 1 shows that the novel protease has a much higher stability in solutions containing sodium hypochlorite than known proteases: The novel protease has a residual activity of 30% in a detergent solution containing 10 ppm NaOCl, whereas known proteases have absolutely no activity under these conditions.

EXAMPLE 3

The stability performance tests were also conducted in 1.1 g/l of a commercial American powder detergent dissolved in approx. 6° dH (German Hardness) water with 1% of Proxan (39.5% $CH_3COOOH$, 4.5% $H_2O_2$, 44% $CH_3COOH$, 11.3% $H_2O$, 0.7% $H_2SO_4$) at 25° C., isothermally for 60 minutes, with a protease concentration of 0.3 CPU per litre.

The results of these tests are shown in table 2 below:

TABLE 2

| Enzyme | Residual Activity |
|---|---|
| Alcalase | 25% |
| Primase | 20% |
| Esperase | 20% |
| Savinase | 25% |
| Durazyme | 85% |
| NOVEL PROTEASE | 100% |

Table 2 shows that the novel protease has a higher stability in solutions containing Proxan than known proteases.

EXAMPLE 4

Wash Performance

The wash performance tests were accomplished on grass soiled cotton, at 20° C., isothermally for 10 minutes.

The tests were performed at enzyme concentrations of 0.0025, 0.005, 0.010, 0.050, 0.1, 0.2 and 0.5 CPU per litre.

2.0 g/l of a commercial American powder detergent were used. The detergent was dissolved in approx. 6° dH (German Hardness) water, and pH was adjusted to 9.5. The textile/wash liquor ratio was 6 g of textile per litre of wash liquor.

Subsequent to washing, the cloths were flushed in running tap water and air-dried. The remission (%R) at 460 nm was determined.

As a measure of the wash performance differential remission, ΔR, was used being equal to the remission after wash with enzyme added, minus the remission after wash with no enzyme added.

The results of these tests are shown in Table 3 below (mean of 2 tests):

TABLE 3

| NOVEL PROTEASE CONCENTRATION CPU/l | ΔR |
|---|---|
| 0.0025 | 3.8 |
| 0.005 | 6.6 |
| 0.010 | 6.4 |
| 0.050 | 11.8 |
| 0.1 | 12.9 |
| 0.2 | 13.6 |
| 0.5 | 13.1 |

Table 3 shows that the novel protease is well suited for use as a detergent enzyme.

I claim:

1. A protease derived from the strain Bacillus sp., DSM 8473, having the following properties:
    (a) an apparent molecular weight of approximately 30 kD as determined by SDS-PAGE;
    (b) an isoelectric point of about 8.8 as determined by isoelectric focusing on LKB Ampholine PAG plates;
    (c) optimum activity at a temperature in the range from 50° C. to 60° C., determined at pH 9.5 with casein as substrate;
    (d) more than 80% activity at a pH in the range of 6–11 when measured at 25° C. with casein as substrate; and
    (e) a residual activity of at least 80% after 60 minutes at 25° C. in 5 ppm hypochlorite relative to the activity of the protease in the absence of 5 ppm hypochlorite.

2. A detergent additive comprising the protease according to claim 1, provided in the form of a non-dusting granulate, a stabilized liquid, a slurry, or a protected enzyme.

3. The process for washing a soiled fabric, comprising treating the soiled fabric with the detergent additive according to claim 2.

4. A detergent composition comprising the protease according to claim 1 and a surfactant.

5. The detergent composition according to claim 4, which further comprises one or more other enzymes selected from the group consisting of amylase, lipase, cutinase, cellulase and oxidoreductase.

6. A process for washing a soiled fabric, comprising treating the soiled fabric with the detergent composition according to claim 4.

7. A process for producing the protease according to claim 1, comprising
    (a) cultivating said strain of Bacillus sp. in a suitable medium, containing carbon and nitrogen sources and inorganic salts, wherein said strain is Bacillus sp., DSM 8473, or a mutant or a variant thereof which produces a protease having the same properties as the protease of claim 1; and
    (b) recovering the protease.

* * * * *